United States Patent [19]

Micheli

[11] 4,130,011

[45] Dec. 19, 1978

[54] FLARED SONIC END NOZZLE VELOCITY COUPLING TEST BURNER

[75] Inventor: Paul L. Micheli, Sacramento, Calif.

[73] Assignee: The United States of America as represented by the Secretary of the Air Force, Washington, D.C.

[21] Appl. No.: 806,437

[22] Filed: Jun. 14, 1977

[51] Int. Cl.² .............................................. G01N 33/22
[52] U.S. Cl. ................................................... 73/35
[58] Field of Search ....................... 73/35, 167; 60/254

[56] References Cited

U.S. PATENT DOCUMENTS

| | | | |
|---|---|---|---|
| 3,701,278 | 10/1972 | Askins et al. | 73/35 |
| 3,788,126 | 1/1974 | Price et al. | 73/35 |
| 3,908,358 | 9/1975 | Sutton et al. | 60/254 |

*Primary Examiner*—James J. Gill
*Attorney, Agent, or Firm*—Joseph E. Rusz; Jacob N. Erlich

[57] ABSTRACT

A flared sonic end nozzle velocity coupling test burner having a body, the walls of which define a chamber. The chamber is closed at one end thereof and has a flared sonic nozzle at the other end. Tests are performed for determining velocity coupling response with a propellant driver located adjacent to the closed end of the chamber and the propellant sample being situated during a first test at approximately the quarter length position and during the second test at approximately the three quarter length position.

9 Claims, 2 Drawing Figures

FLARED SONIC END NOZZLE VELOCITY COUPLING TEST BURNER

STATEMENT OF GOVERNMENT INTEREST

The invention described herein may be manufactured and used by or for the Government for governmental purposes without the payment of any royalty thereon.

BACKGROUND OF THE INVENTION

This invention relates generally to test burners for rockets, and more particularly to a test burner having a flared end vent or nozzle and which is capable of measuring velocity coupled response of solid propellants.

Combustion instability is a phenomenon which occurs readily under a wide variety of conditions throughout rocketry design. This instability can result in a mild vibration, a severe vibration of the rocket, or in extreme conditions, to complete motor failure. The instability usually couples with an acoustic mode of the rocket chamber and exhibits itself as a pressure oscillation. Velocity coupling is usually associated with the axial mode of the combustion chamber.

Basically the burning rate of a solid propellant utilized in rockets depends upon the pressure and gas velocity. When the pressure or gas velocity oscillates in time, the propellant burning rate attempts to accommodate itself to the changing conditions, and this ability is called its response. The response is basically a dimensionless ratio of the fluctuating burning rate to the fluctuating pressure or to the gas velocity. The latter ratio is also known as the velocity coupled response.

Despite the adverse effects velocity coupling instability produces on rockets and missiles, the present state of the art is inadequate to minimize its occurrence. In fact, in many instances this velocity coupling instability is not even considered a factor in rocket design until its presence is detected from firing of the rocket motor. Attempts to alleviate this problem after the fact are usually expensive and ineffective.

Test burners have been designed which have attempted to detect the presence of velocity coupled instability. In such systems presently in use a baseline or reference test is conducted and a propellant sample is then added in order to determine what changes occur because of the sample. The procedure is quite complicated because of two reasons, one is analytical in nature and the other experimental.

Within the prior art test burners, the sample is located to maximize the velocity coupling effect, which however, also places the sample at a location where the pressure coupling and dynamic pressure drop (flow turning) effects are significant. In such a procedure the sample contributions are all additive. The analytical problem of unraveling the velocity coupling in the presence of these other two processes has heretofore never been solved, and, in fact, could not be solved by the prior art, and, therefore a value for flow turning had to be assumed. The experimental problem is that the sample location not only excites the first acoustic mode but also the third mode. It is this latter mode which turns out to interfere with the first mode, the interference mechanism being through amplitude dependent gas dynamic processes. It has therefore been necessary in the past that the pressure amplitude of higher modes be negligible in order to validly measure the velocity response.

SUMMARY OF THE INVENTION

The instant invention sets forth a velocity coupled test burner which solves the problems set forth hereinabove. The test burner is of an elongated configuration having a flared end vent region or nozzle in order to reduce nozzle losses. In addition, a single fore end driver grain or propellant is used as a base line rather than dual grains at both ends of the burner chamber as in the past. Furthermore, the nozzle which includes a flared region to reduce nozzle losses is sonic rather than subsonic, and, as pointed out hereinabove, is located at the aft end of the test burner. In its operation the sonic end vent test burner of this invention is capable of measuring velocity coupling response directly without a knowledge of the pressure coupled response or dynamic pressure drop (flow turning). Since both these processes need not be measured the number of tests required with the sonic end vent burner of this invention is substantially reduced. With the end vent test burner, a sample can be located at the center of the burner and elicit only flow turning if such flow turning is present.

It has been shown that the sonic end vent test burner of this invention tends to dampen out the higher modes, however, with non-metallized propellants there is still a tendancy to excite the second or third mode. The excitation of these modes can be reduced substantially and even eliminated by moving the sample from the quarter to the one-sixth length location. Further, the use of the flared end vent or nozzle tends to dampen the higher modes and therefore generally tends to show only first mode content.

It is therefore an object of this invention to provide a test burner for reliably ascertaining velocity coupling response of solid propellants.

It is another object of this invention to provide a test burner which incorporates in its construction a flared end nozzle or vent and thereby eliminates the prior knowledge of pressure coupled response or flow turning for its operation.

It is a further object of this invention to provide a test burner which utilizes a sonic rather than subsonic nozzle.

It is still a further object of this invention to provide a test burner which uses only a single driver located at one end of the burner.

It is still another object of this invention to provide a test burner which is economical to produce as well as operate and which utilizes conventional, currently available components in its construction that lend themselves to standard mass producing manufacturing techniques.

For a better understanding of the present invention together with other and further objects thereof, reference is made to the following description taken in conjunction with the accompanying drawing and its scope will be pointed out in the appended claims.

DETAILED DESCRIPTION OF THE PREFERRED EMBODIMENT

Figure 1:
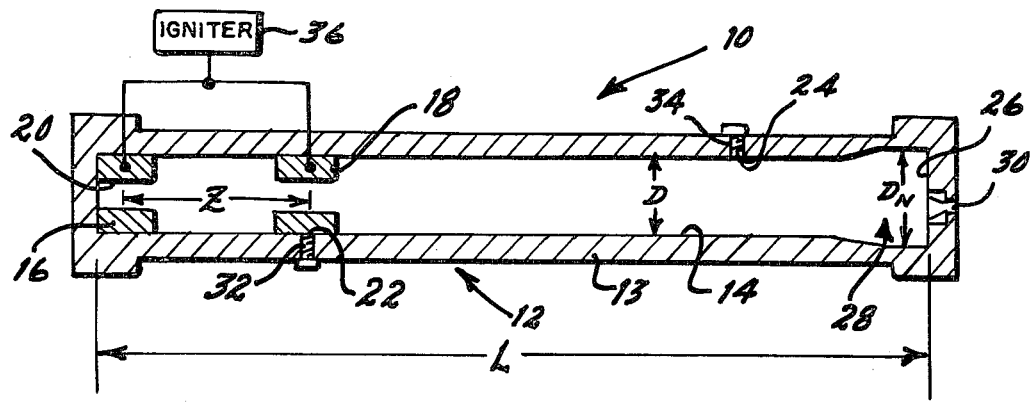
FIG. 1 represents a schematic side elevational view, shown partly in cross-section, of the flared end nozzle velocity coupling test burner of this invention with the sample located in its fore end position.

The principal notion involved in velocity coupling that clearly discriminates it from pressure coupling is that the driving force is independent of flow velocity direction. The time-wise pressure-velocity relationships imposed by this requirement eventually leads to a model description of $I_{vc}$ (velocity coupling) wherein:

$$I_{vc} \sim F\{|\bar{u} + u'| - \bar{u}\}/u'$$

It is emphasized that the Fourier transform of $|\bar{u} + u'|$ has to be experimentally evaluated and this necessitates that the experiments be conducted under two separate conditions, i.e., for positive $u'$ and for negative $u'$ where $u$ is the mainstream velocity and $\bar{u}$ is its steady state value while $u'$ is its fluctuating value. Only then is the driving, which is independent of velocity direction, obtained. Such an analysis therefore leads to the conclusion that the sign of $I_{vc}$ should be changed to simulate the effect of the Fourier decomposition of the perturbation velocity. For the real phenomenon of velocity coupling, $I_{vc}$ may depend on the flux perturbation $p'$ and $u'$ where $p'$ is the fluctuating value of pressure. Because the exact nature of velocity coupling can only be analytically approximated, the best experimental simulation is achieved by evaluating the change in driving associated with the change in sample location using the sonic flared end vent or nozzle test burner 10 of this invention shown in FIGS. 1 and 2 of the drawing. In this way the experiment simulates the analytical representation which is defined as velocity coupling.

Reference is now made to FIG. 1 of the drawing which clearly shows the flared end nozzle test burner 10 of this invention. Burner 10 is constructed, preferably, of an elongated cylindrically shaped body 12 of any suitable rocket or burner material having walls 13 which encompass the interior or chamber 14 of test burner 10. Located within chamber 14 is a propellant driver 16 as well as a propellant sample 18 made of any suitable solid rocket propellant such as composed of HTPB and $NH_4ClO_4$. Driver 16 is situated at the fore-end 20 of burner 10 while sample 18 may be situated at a pair of locations 22 and 24 within chamber 14 in a position more fully described in detail hereinbelow.

The fore-end 20 of burner 10 of this invention is enclosed while the aft-end 26 of burner 10 is formed in the shape of a flared region 28 having a centrally located sonic nozzle end vent or opening 30. In addition to nozzle 30, a pair of conventional transducers 32 and 34 are mounted within walls 13 of body 12 adjacent propellant samples 18 at positions 22 and 24. Transducers 32 and 34 are operatively connected to samples 18 in order to provide sufficient test data to be utilized in an accurate measurement of velocity coupling response.

The overall chamber length is designated as L and can vary depending upon the test frequency. The length, L, however, generally has a nominal value of 24 inches. The inner diameter, D, of chamber 14 is approximately 1.5 inches for typical test conditions. Located approximately 2 inches from the aft-end 26 of burner 10 is the flared region 28. Flared region 28 has a diameter, $D_n$, of approximately 2 inches at its flared portion terminating in centrally located vent or opening 30.

For optimum operability and test results, sample 18 as well as transducers 32 and 34 are situated at positions within chamber 14 wherein a relationship Z/L is established at approximately 0.16 to 0.25 (shown in FIG. 1) and 0.75 (shown in FIG. 2) where Z is the distance the center of sample 18 is situated from the center of driver 16 and L is the overall length of chamber 14 of test burner 10 of this invention. Ignition of the propellant driver 16 and samples 18 are accomplished by any conventional propellant ignition system 36 either independently as shown in FIG. 2 or in combination as shown in FIG. 1.

Figure 2:
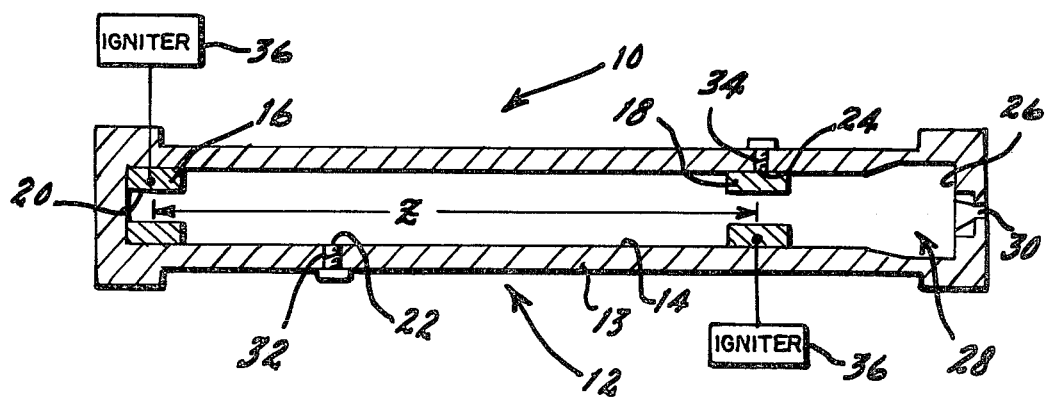
FIG. 2 represents a schematic side elevational view, shown partly in cross-section, of the flared end nozzle velocity coupling test burner of this invention with the sample located in its aft-end position.

During operation tests are performed first with propellant sample 18 at location 22 as shown in FIG. 1 and second with sample 18 at position 24 as shown in FIG. 2. It is necessary that a relationship be maintained of Z/L = 0.16 or 0.25 for the first test and Z/L = 0.83 or 0.75 for the second test for accurate measurements of velocity coupling response. It is furthermore extremely important that the tests be initiated with the simultaneous ignition of driver 16 and sample 18 by igniter 36. In addition a ratio, $A_r$, of the area of the propellant surface to the flow area of the propellant grain section should be between 2 to 6.

The sonic nozzle approach of this invention utilizes a baseline or initial condition and a sample 18 which is located at two positions. Two tests are generally run; in one test sample 18 is located at substantially quarter length, in the second test at the three-quarter length. The difference in results between the two tests is determined. In this way, the pressure coupling and flow turning effects cancel and leave only the velocity coupling contribution. With the instant invention it is possible to situate a sample at the center of the chamber to elicit only flow turning, if present.

The sonic end vent 30 tends to dampen out the higher modes. But even so, with non-metallized propellants there is still a tendency to excite the second or third mode. The excitation of these modes can be reduced and even eliminated by moving sample 18 from the quarter to one-sixth length location (Z/L = 0.16). Further, the use of a flared nozzle 28 tends to dampen the higher modes more than the first mode and hence the test burner 10 of this invention generally tends to show only first mode content. Another important advantage of this invention is economic in nature. The data from the instant invention are obtained over a broad pressure range and the velocity coupled response can be obtained as a function of pressure with fewer tests than in prior art equipment.

Although this invention has been described with reference to a particular embodiment it will be understood to those skilled in the art that this invention is also capable of a variety of alternate embodiments within the spirit and scope of the appended claims.

I claim:

1. A velocity coupling test burner comprising an elongated body, said body having walls which define a chamber formed within said body, said chamber being closed at one end thereof and having a flared nozzle formed at the other end thereof, said flared nozzle terminating in a centrally located opening, a propellant driver located within said chamber adjacent the closed end thereof, first and second transducers located within said walls of said body, each of said transducers being capable of operably attaching a propellent sample thereto, and means operably connected to said driver and said sample for igniting said driver and said sample, whereby upon ignition of said propellant driver and said propellant sample the velocity coupling response can be measured.

2. A velocity coupling test burner as defined in claim 1 wherein said chamber has an inner diameter of approximately 1½ inches.

3. A velocity coupling test burner as defined in claim 2 wherein said flared nozzle has an inner diameter of approximately 2 inches at its flared portion.

4. A velocity coupling test burner as defined in claim 3 wherein said flared nozzle has a length of approximately 2 inches.

5. A velocity coupling test burner as defined in claim 4 wherein said first transducer is located at a distance of approximately 0.25 of the length of said chamber from said closed end.

6. A velocity coupling test burner as defined in claim 5 wherein said second transducer is located at a distance of approximately 0.75 of the length of said chamber from said closed end.

7. A velocity coupling test burner as defined in claim 6 wherein the overall length of said chamber is approximately 24 inches.

8. A velocity coupling test burner as defined in claim 7 wherein said propellant utilized for said driver and said sample are the same composition.

9. A velocity coupling test burner as defined in claim 4 wherein said first transducer is located at a distance of approximately 0.16 of the length of said chamber from said closed end.

* * * * *